United States Patent

Wallace

[11] Patent Number: 5,101,834
[45] Date of Patent: Apr. 7, 1992

[54] BREATHING CIRCUIT WITH SLIDABLE GAS SAMPLING TUBE

[75] Inventor: Dean R. Wallace, Fort Myers, Fla.
[73] Assignee: Intertech Resources Inc., Lincolnshire, Ill.
[21] Appl. No.: 662,839
[22] Filed: Mar. 1, 1991
[51] Int. Cl.⁵ .................. A61B 5/08; B23P 11/02
[52] U.S. Cl. .................. 128/719; 29/447; 29/450
[58] Field of Search ........... 29/450, 443, 446, 447, 29/512; 128/716, 717, 718, 719

[56] References Cited

U.S. PATENT DOCUMENTS

| | | | |
|---|---|---|---|
| 3,880,591 | 4/1975 | Burroughs | 128/719 X |
| 4,221,130 | 9/1980 | Burrows | 128/719 X |
| 4,446,869 | 5/1984 | Knodle | 128/719 X |
| 4,546,778 | 10/1985 | Sullivan | 128/719 X |
| 4,723,543 | 2/1988 | Beran | 128/719 X |
| 4,991,591 | 2/1991 | Jones et al. | 128/719 |

Primary Examiner—Joseph M. Gorski
Assistant Examiner—Peter Dungba Vo
Attorney, Agent, or Firm—Marshall, O'Toole, Gerstein, Murray & Bicknell

[57] ABSTRACT

A tubular adapter is formed by a wall, the wall having a hole formed therein, and a gas sampling tube extends through the hole. The respective diameters of the hole and the tube are sized to produce a tight sealed connection therebetween but permit adjustment of the tube in the hole. The sampling tube has a sampling end thereof located within the tubular adapter, and the sampling end has a radially enlarged or flanged portion which is larger than the hole, whereby the sampling tube may be adjusted in the hole but may not be withdrawn.

8 Claims, 1 Drawing Sheet

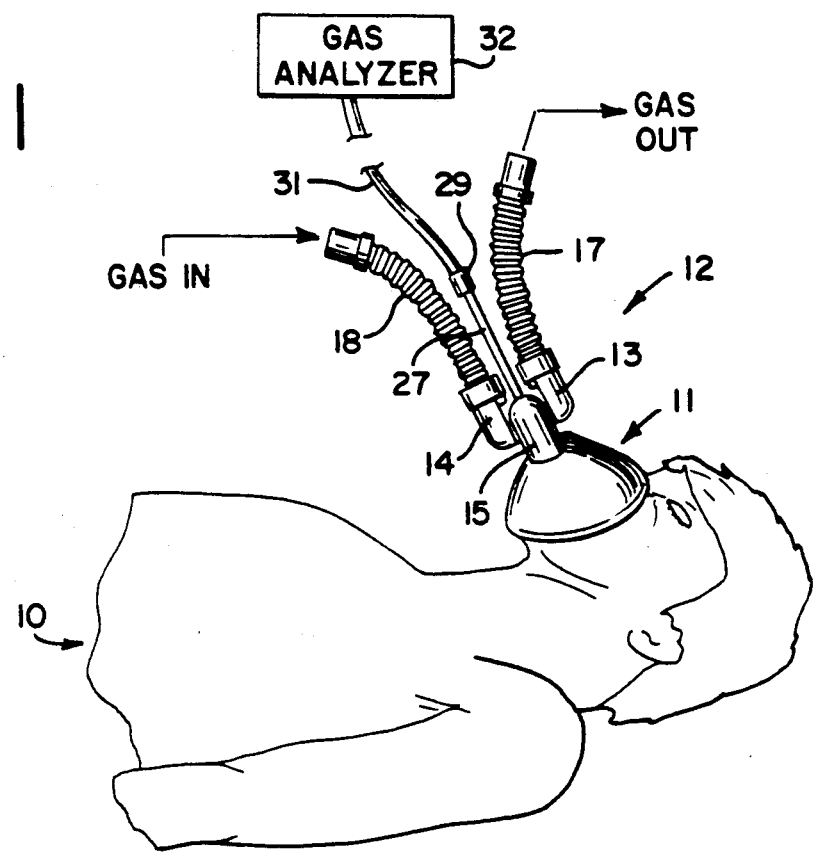
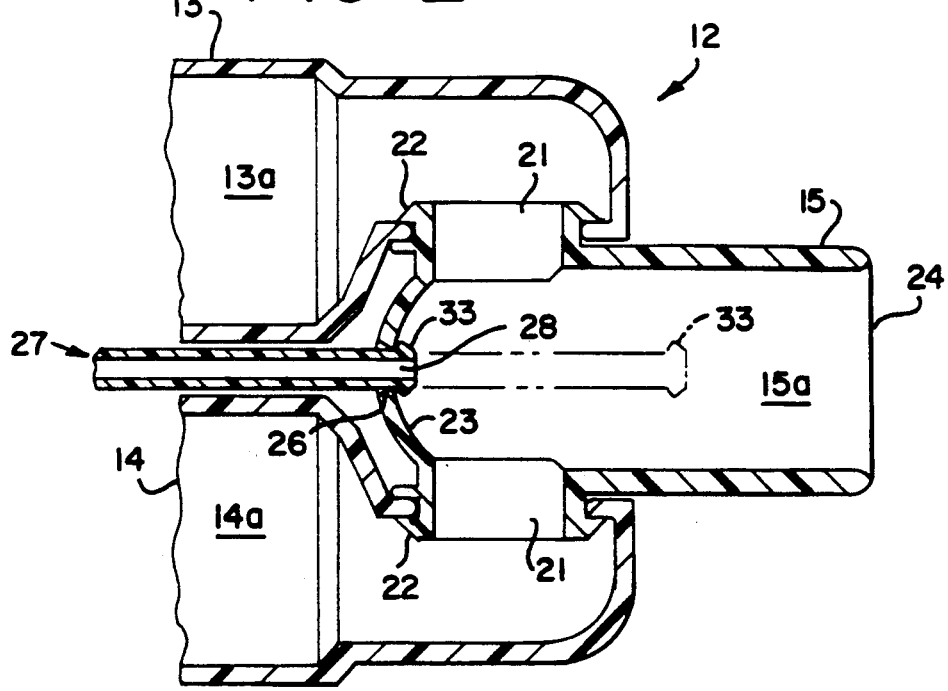

BREATHING CIRCUIT WITH SLIDABLE GAS SAMPLING TUBE

FIELD AND BACKGROUND OF THE INVENTION

This invention relates to a breathing circuit for a patient, and more particularly to a gas sampling tube of a respirator or anesthesia system.

Respiratory therapy and anesthesia systems include an inhalation tube for conducting fresh gas to a patient and an exhalation tube for conducting gas away from the patient. The two tubes are usually joined to a Y-piece which in turn is coupled to a face mask or a trach tube. Such a system may also include a gas sampling tube which removes samples of the gas and feeds the samples to a gas analyzer. In a respiratory therapy system, the $CO_2$ in the gas is analyzed, and in an anesthesia system a number of gases may be analyzed.

Numerous prior art patents show such systems, and the following is a list of U.S. Pat. Nos. relating to breathing systems:

| U.S. Pat. No. | Patentee | Date |
| --- | --- | --- |
| 4,914,720 | KNODLE ET AL. | 04-03-90 |
| 4,852,563 | GROSS | 08-01-89 |
| 4,850,371 | BROADHURST ET AL. | 07-25-89 |
| 4,846,167 | TIBBALS | 07-11-89 |
| 4,840,172 | AUGUSTINE ET AL. | 06-20-89 |
| 4,827,921 | RUGHEIMER | 05-09-89 |
| 4,821,736 | WATSON | 04-18-89 |
| 4,815,459 | BERAN | 03-28-89 |
| 4,774,940 | LINDER | 10-04-88 |
| 4,677,987 | CHOKSI | 07-07-87 |
| 4,637,384 | SCHROEDER | 01-20-87 |
| 4,621,634 | NOWACKI ET AL. | 11-11-86 |
| 4,558,709 | AIDA ET AL. | 12-17-85 |
| 4,558,708 | LABUDA | 12-17-85 |
| 4,456,014 | BUCK ET AL. | 06-26-84 |
| 4,346,584 | BOEHRINGER | 08-31-82 |
| 4,297,871 | WRIGHT ET AL. | 11-03-81 |
| 4,221,130 | BURROWS | 09-09-80 |
| 4,202,352 | OSBORN | 05-13-80 |
| 4,197,858 | OSBORN | 04-15-80 |
| 4,178,919 | HALL | 12-18-79 |
| 3,927,670 | TURNEY ET AL. | 12-23-75 |
| 3,910,261 | RAGSDALE ET AL. | 10-07-75 |

The P.V. Choksi U.S. Pat. No. 4,677,987, for example, shows a variety of structures including a sampling tube, wherein the sampling tube extends through the wall of a gas tube of a breathing circuit. FIG. 2 of this patent shows a sampling tube pressed through a hole formed in an elbow and extending along the axis of one arm of the elbow.

In such a system it is an advantage to be able to adjust the position of the sampling tube to obtain an accurate measurement or analysis of both the inhaled and exhaled gases. It is also important that the system be inexpensive and have a minimum risk of harming the patient.

It is therefore a general object of the present invention to provide an improved arrangement of a gas sampling tube in a breathing system.

SUMMARY OF THE INVENTION

Apparatus in accordance with this invention comprises a tubular adapter formed by a wall, the wall having a hole formed therein, and a gas sampling tube extending through the hole. The respective diameters of the hole and the sampling tube are sized to produce a tight sealed connection therebetween but to permit adjustment of the tube in the hole. The sampling tube has a sampling end thereof located within the tubular adapter, and the sampling end has a radially enlarged or flanged portion which is larger than the hole, whereby the sampling tube may be adjusted in the hole but may not be withdrawn.

DETAILED DESCRIPTION OF THE DRAWINGS

The invention will be better understood from the following detailed description taken in conjunction with the accompanying FIGURES of the drawing, wherein:

FIG. 1 is a perspective view of apparatus incorporation the present invention; and FIG. 2 is an enlarged sectional view of a fragment of the apparatus of FIG. 1.

DETAILED DESCRIPTION OF THE DRAWINGS

FIG. 1 illustrates the construction and use of the apparatus with a patient 10. A face mask 11 is in position over the mouth and nose of the patient, although it should be understood that a trach tube could be used instead.

An adapter 12 is connected to the face mask 11, the adapter being formed by a Y-piece which includes two legs 13 and 14 and a center leg 15. The center leg 15 is coupled to the face mask 11 and carries both inhaled and exhaled gases, whereas flexible corrugated tubes 17 and 18 are connected to the two legs 13 and 14. In the present specific example, the tube 18 is connected to a source of inhaled gas and the tube 17 is connected to a receptacle or receiver of exhaled gas.

In the specific example illustrated and described herein, the three legs 13–15 are formed by thin walled circular tubes, the walls being indicated by the numerals 13a, 14a and 15a respectively. The axes of the three legs may be parallel or the two legs 13 and 14 may be swiveled on the center leg 15. Flow openings 21 are formed on opposite sides of the wall 15a, and the legs 13 and 14 are mounted on flanges 22 surrounding the openings 21, such that the legs 13 and 14 may be swiveled on the axes of the openings 21.

The center leg 15 further includes a semispherical end wall 23 on its end which is opposite to the open end 24 connected to the face mask 11. A hole 26 is formed through the wall 23 at substantially its center, the hole 24 preferably being coaxial with the wall 15a in the specific example illustrated wherein the adapter comprises a Y-piece.

A gas sampling tube 27 having a relatively small diameter (for example, the O.D. is typically 0.125 inch and the I.D. is typically 0.025 to 0.06 inch) is positioned in the hole 26, and has an inner or sampling end 28 which is within the interior of the center leg 24. The outer end of the tube 27 has a coupler 29 fastened to it which is connected to a tube 31 that leads to a gas analyzer 32.

The sampling tube 27 is made of a flexible somewhat pliable material such as plastic, and its outer diameter is sized relative to the size of the hole 26 such that the margin of the hole tightly pinches the tube 27. This pinching engagement serves both to hold the tube 27 in a selected or adjusted position relative to the leg 15 and to form a gas seal between the wall 23 and the tube 27.

The hole 26 may have a straight or constant diameter bore or the bore may be cone shaped to produce a relatively thin annular line of contact between the tube 27 and the wall 23.

While there is a tight pinch engagement between the wall 23 and the tube 27, the plastic parts are pliable to permit the position of the tube 27 to be adjusted within the center leg 15. FIG. 2 shows one position in solid lines and another position in dash-dot lines, and it will be obvious that the tube 27 may be located between these two positions or the sampling end 28 may be located closer to the end 24 and the patient. As shown in FIG. 2, the axes of the hole 26 and the tube 27 are on the axis of the tubular wall 15a.

To prevent the sampling tube 27 from being accidentally pulled out of the hole 26, a flange or radially enlarged portion 33 is formed on the sampling end 28. The flange 33 is integral with the tube 27 and has a larger diameter than the hole 26, thereby retaining the tube connected with the leg 15. The flange may be formed by briefly heating the plastic end 28 to soften it and cause the end to form the flange.

The sampling tube 27 and the Y-piece adapter 12 are made of molded plastic which is sufficiently rigid to maintain their shape but pliable enough that the tube 27 forms a pinch seal with the adapter 12 but that the tube position may be adjusted. A suitable plastic for the Y-piece is a low density polyethylene. The sampling tube 27 may be made of PVC having a hardness of 90-100 Durometer on the Shore A scale. The tube 27 should be pliable enough that it may be bent and pinched at the margin of the hole 26, but at the same time not so pliable that the flange 33 may be pulled or extruded through the hole 26. The end of a PVC tube naturally flairs outwardly (not inwardly) when heated without pressure being applied to the end.

It will be apparent from the foregoing that a novel, useful and improved gas sampling arrangement has been provided. The sampling tube 27 is connected directly to the Y-piece 12 which is normally provided in such a circuit and not to a special adapter designed for use only with a sampling tube, and therefore a part is eliminated. This is advantageous because of the cost savings and because a point of potential leakage (at the ends of a special adapter) is avoided. Further, the absence of a special adapter reduces the amount of dead air space.

The location of the sampling end 28 may be adjusted in the Y-piece to obtain the optimum location for an accurate sample of the gases flowing to and from the patient, and to reduce the amount of dead space between the patient and the sampling end 28 to obtain an accurate gas sample. Since the tube 27 slides along the axis of the leg 15, it is equidistant from both openings 21, thereby attaining a balance between the gases in the two legs 13 and 14.

While the tube 27 may be slid through the hole 26, it cannot accidentally be pulled out of the hole 26 because the flange 33 prevents withdrawal. The flange 33 is integral with the tube 27 and is not a separate part which would have the potential danger of coming loose and harming a patient.

What is claimed is:

1. A gas sampling apparatus for a breathing circuit, comprising an adapter for connection in a breathing circuit and having respiratory gases flowing therethrough, said adapter including an adapter wall which forms a gas flow passage, a hole formed through said wall, and a gas sampling tube which extends through said hole, said wall at the margin of said hole engaging said sampling tube in a pinch fit connection, said connection forming a seal but allowing sliding movement of said sampling tube in said hole, said sampling tube having an open sampling end which is located internally of said wall and in communication with the respiratory gases in said passage, and enlarged means on said sampling tube which prevents said sampling end from accidentally sliding out of said hole.

2. Apparatus as set forth in claim 1, wherein said means comprises a radially enlarged portion formed integrally with said sampling tube.

3. Apparatus as set forth in claim 2, wherein said enlarged portion is formed by a radial flange.

4. Apparatus as set forth in claim 2, wherein said enlarged portion is formed closely adjacent said sampling end.

5. Apparatus as set forth in claim 1, wherein said adapter wall forms a tube which is open at one end and is closed by an end wall at the other end, and said hole and said sampling tube extend through said end wall.

6. Apparatus as set forth in claim 5, wherein said tube has a centrally located axis, and said hole and said tube are located on said axis.

7. Apparatus as set forth in claim 6, wherein the location of said sampling end is adjustable along said axis.

8. Apparatus as set forth in claim 1, wherein said adapter wall forms one leg of Y-piece, said adapter wall further having two openings formed therein for connection with two additional legs, and said sampling tube being located substantially equidistant from said two openings.

* * * * *